US011191591B2

(12) United States Patent
Moeskops et al.

(10) Patent No.: US 11,191,591 B2
(45) Date of Patent: Dec. 7, 2021

(54) HAIR CUTTING DEVICE AND A METHOD OF OPERATING A HAIR CUTTING DEVICE

(71) Applicant: KONINKLIJKE PHILIPS N.V., Eindhoven (NL)

(72) Inventors: Bastiaan Wilhelmus Maria Moeskops, Eindhoven (NL); Mark Thomas Johnson, Eindhoven (NL); Marius Iosif Boamfa, Eindhoven (NL); Kiran Kumar Thumma, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 463 days.

(21) Appl. No.: 16/317,938

(22) PCT Filed: Jul. 26, 2017

(86) PCT No.: PCT/EP2017/068819
§ 371 (c)(1),
(2) Date: Jan. 15, 2019

(87) PCT Pub. No.: WO2018/024552
PCT Pub. Date: Feb. 8, 2018

(65) Prior Publication Data
US 2021/0282852 A1 Sep. 16, 2021

(30) Foreign Application Priority Data
Aug. 5, 2016 (EP) .................................... 16183040

(51) Int. Cl.
A61B 18/20 (2006.01)
A61B 18/00 (2006.01)
(Continued)

(52) U.S. Cl.
CPC .. *A61B 18/203* (2013.01); *A61B 2017/00075* (2013.01); *A61B 2018/00476* (2013.01);
(Continued)

(58) Field of Classification Search
CPC ........ A61B 18/203; A61B 2017/00075; A61B 2018/00476; A61B 2018/00601;
(Continued)

(56) References Cited

U.S. PATENT DOCUMENTS 5,182,857 A 2/1993 Simon
9,017,322 B2 * 4/2015 Gustavsson .......... A61B 18/203
606/36

(Continued)

FOREIGN PATENT DOCUMENTS

WO 9533600 A1 12/1995
WO 2014143670 A1 9/2014

OTHER PUBLICATIONS

M.D. Greenwell, A. Willner, Paul L. Kirk: Human AAIR Studies: III. Refractive Index of Crown Hair, 31 Am. Inst. Crim. L. & CRIMINOLOGY 746 (1940-1941).

*Primary Examiner* — Jonathan T Kuo

(57) ABSTRACT

There is provided a hair cutting device for cutting hair on a body of a subject, the hair cutting device comprising a light source for generating light at one or more specific wavelengths corresponding to wavelengths absorbed by one or more chromophores in or on hair; a cutting element that comprises an optical waveguide that is coupled at a first end to the light source to receive light, wherein a portion of a sidewall of the optical waveguide forms a cutting face for contacting hair; a light sensor that is coupled to the optical waveguide away from the first end, wherein the light sensor is for measuring the light level in the optical waveguide and for providing an output signal representing the measured light level; and a control unit that is coupled to the light (Continued)

source, and coupled to the light sensor to receive the output signal, wherein the control unit is configured to determine a measure of the amount of input light transmitted across the optical waveguide from the measured light level and an input light level at the first end of the optical waveguide; and to control the power of the light generated by the light source based on the determined measure.

15 Claims, 7 Drawing Sheets

(51) Int. Cl.
*A61B 18/22* (2006.01)
*A61B 17/00* (2006.01)

(52) U.S. Cl.
CPC ............... *A61B 2018/00601* (2013.01); *A61B 2018/00702* (2013.01); *A61B 2018/2255* (2013.01)

(58) Field of Classification Search
CPC .. A61B 2018/00702; A61B 2018/2255; A61B 18/20–18/28; A61N 5/06–2005/073
See application file for complete search history.

(56) References Cited

U.S. PATENT DOCUMENTS

| | | | |
|---|---|---|---|
| 9,532,834 B2* | 1/2017 | Gustavsson | A61B 18/203 |
| 2012/0123444 A1 | 5/2012 | Verhagen | |
| 2013/0072803 A1 | 3/2013 | Altshuler | |
| 2014/0276685 A1* | 9/2014 | Gustavsson | A61B 18/203 |
| | | | 606/9 |
| 2015/0173826 A1 | 6/2015 | Churchill | |
| 2015/0173835 A1 | 6/2015 | Moeskops | |
| 2015/0223889 A1* | 8/2015 | Gustavsson | A61B 18/22 |
| | | | 606/9 |
| 2016/0107323 A1 | 4/2016 | Krans | |
| 2018/0140357 A1* | 5/2018 | Moeskops | A61B 18/203 |

* cited by examiner

HAIR CUTTING DEVICE AND A METHOD OF OPERATING A HAIR CUTTING DEVICE

This application is the U.S. National Phase application under 35 U.S.C. § 371 of International Application No. PCT/EP2017/068819, filed on Jul. 26, 2017, which claims the benefit of International Application No. 16183040.1 filed on Aug. 5, 2016. These applications are hereby incorporated by reference herein.

FIELD OF THE INVENTION

The invention relates to a hair cutting device for cutting (e.g. shaving) hair on a body of a subject, and in particular relates to a hair cutting device that uses light to cut or shave hair and a method of operating a hair cutting device.

BACKGROUND OF THE INVENTION

Shaving devices for cutting or shaving hair on a body of a subject typically make use of one or more blades that cut hairs as the blade is moved across the skin of the subject. The blades can be static within the device, for example as in a wet razor, whereas in other types of devices, for example electric shavers, one or more blade elements can be actuated (e.g. rotated or oscillated) in order to produce a cutting action.

However, an alternative type of shaving device has been proposed in WO 2014/143670 that makes use of laser light. In particular a laser light source is provided that is configured to generate laser light having a wavelength selected to target a predetermined chromophore to effectively cut a hair shaft. A fiber optic is located on a shaving portion of the device that is positioned to receive the laser light from the laser light source at a proximal end, conduct the laser light from the proximal end toward a distal end, and emit the light out of a cutting region of the fiber optic and toward hair when the cutting region is brought in contact with the hair.

To achieve good shaving effectiveness, the cutting element of the shaving device (i.e. the fiber optic in the case of the device in WO 2014/143670) needs to be brought very close to the skin and the laser light needs to have sufficient power to cut the hair through melting. However, light can couple into the skin if the cutting element is brought into contact with the skin, and light at the power required to melt hair can burn or irritate the skin, and this creates a significant safety issue for this type of shaving device.

Therefore there is a need for an improved hair cutting device that reduces the risk of damage or injury to the skin of the subject and that maintains hair cutting effectiveness.

SUMMARY OF THE INVENTION

According to a first aspect, there is provided a hair cutting device for cutting hair on a body of a subject, the hair cutting device comprising a light source for generating light at one or more specific wavelengths corresponding to wavelengths absorbed by one or more chromophores in or on hair; a cutting element that comprises an optical waveguide that is coupled at a first end to the light source to receive light, wherein a portion of a sidewall of the optical waveguide forms a cutting face for contacting hair; a light sensor that is coupled to the optical waveguide away from the first end, wherein the light sensor is for measuring the light level in the optical waveguide and for providing an output signal representing the measured light level; and a control unit that is coupled to the light source, and coupled to the light sensor to receive the output signal, wherein the control unit is configured to determine a measure of the amount of input light transmitted across the optical waveguide from the measured light level and an input light level at the first end of the optical waveguide; and to control the power of the light generated by the light source based on the determined measure. Thus, the invention provides that the risk of irritating or burning skin can be reduced without having to compromise the cutting effectiveness. In particular, the measure of the amount of light transmitted across the optical waveguide provides an indication of whether skin or hair is in contact with the optical waveguide, and the power of the light in the optical waveguide can be controlled accordingly.

In some embodiments, the control unit is configured to receive the input light level at the first end of the optical waveguide from a second light sensor at the first end or an indication of the input light level at the first end from the light source.

In some embodiments, the control unit is configured to set the power of the light generated by the light source to a first power level if the determined measure is above a threshold value, and to set the power of the light generated by the light source to a second power level if the determined measure is less than the threshold value, wherein the first power level is higher than the second power level.

In some embodiments, the control unit is configured to set the power of the light generated by the light source to the first power level if the determined measure is equal to an initial amount.

In some embodiments, the control unit is configured to set the power of the light generated by the light source to the second power level if the determined measure is equal to an initial amount.

In some embodiments, the first power level corresponds to a power level required to melt hair and the second power level corresponds to a power level that does not irritate or burn skin.

In some embodiments, the control unit is further configured to determine if debris is present on the optical waveguide based on the determined measure.

In some embodiments, the control unit is configured to determine a decrease in the determined measure from an initial or default amount of input light transmitted though the optical waveguide on activation of the light source; and to determine that debris is present on the optical waveguide if the magnitude of the decrease from the initial or default amount is greater than a threshold value.

In some embodiments, the hair cutting device further comprises a movement sensor for measuring the speed of movement of the hair cutting device; and the control unit is configured to determine if debris is present on the optical waveguide based on the determined measure and the measured speed of movement.

In some embodiments, the control unit is configured to determine that debris is present on the optical waveguide if the determined measure is below a threshold value and the measured speed of movement is above a speed threshold.

In some embodiments, the light sensor is coupled to the optical waveguide away from the first end such that the portion of the sidewall forming the cutting face is between the light sensor and the first end.

According to a second aspect, there is provided a method of operating a hair cutting device to cut hair on a body of a subject, the hair cutting device comprising a cutting unit that comprises an optical waveguide, wherein a portion of a sidewall of the optical waveguide forms a cutting face for contacting hair, the method comprising generating light using a light source at one or more specific wavelengths corresponding to wavelengths absorbed by one or more chromophores in or on hair; coupling the light from the light source into a first end of the optical waveguide; measuring the light level in the optical waveguide using a light sensor that is coupled to the optical waveguide away from the first end; determining a measure of an amount of input light transmitted through the optical waveguide from the measured light level and an input light level at the first end of the optical waveguide; and controlling the power of the light generated by the light source based on the determined measure.

In some embodiments, the method further comprises the step of receiving the input light level at the first end of the optical waveguide from a second light sensor at the first end or an indication of the light level at the first end from the light source.

In some embodiments, the step of controlling the power of the light comprises setting the power of the light generated by the light source to a first power level if the determined measure is above a threshold value, and setting the power of the light generated by the light source to a second power level if the determined measure is less than the threshold value, wherein the first power level is higher than the second power level.

In some embodiments, the step of controlling the power of the light comprises setting the power of the light generated by the light source to the first power level if the determined measure is equal to an initial amount.

In some embodiments, the step of controlling the power of the light comprises setting the power of the light generated by the light source to the second power level if the determined measure is equal to an initial amount.

In some embodiments, the first power level corresponds to a power level required to melt hair and the second power level corresponds to a power level that does not irritate or burn skin.

In some embodiments, the method further comprises the step of determining if debris is present on the optical waveguide based on the determined measure.

In some embodiments, the step of determining if debris is present comprises determining a decrease in the determined measure from an initial or default amount of input light transmitted though the optical waveguide on activation of the light source; and determining that debris is present on the optical waveguide if the magnitude of the decrease from the initial or default amount is greater than a threshold value.

In some embodiments, the method further comprises the step of measuring the speed of movement of the hair cutting device using a movement sensor; and wherein the step of determining if debris is present on the optical waveguide comprises determining if debris is present on the optical waveguide based on the determined measure and the measured speed of movement.

In some embodiments, the step of determining if debris is present on the optical waveguide comprises determining that debris is present on the optical waveguide if the determined measure is below a threshold value and the measured speed of movement is above a speed threshold.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

As noted above, the present invention provides an improvement in the safety and comfort of a subject that is using a laser light-based shaving device, for example as described in WO 2014/143670. In particular, the light level in the optical waveguide is measured and the power of the light in the optical waveguide is set, adjusted or otherwise controlled on the basis of the measured light level. The measured light level (in combination with an initial or 'no-coupling' light level) provides an indication of the amount of light that is coupling out of the optical waveguide and into another object (e.g. skin, hair, other skin features, such as moles, or debris, such as cut hairs, shaving liquids, etc.), and the amount of light that couples out of the optical waveguide into the other object depends in part on the size of the contact area between the optical waveguide and the object. Thus, since skin and debris typically have a larger contact area with the optical waveguide than hair (e.g. at least an order of magnitude larger), it is possible to determine or estimate whether the optical waveguide is contacting hair or skin or debris based on the amount of light lost across the optical waveguide (or the amount of light transmitted through the optical waveguide), and the power of the light in the optical waveguide can be set accordingly (e.g. lower power in the case of contact with skin or debris and higher power in the case of contact with hair).

It will be appreciated that the invention is applicable to shaving devices (e.g. razors or electric shavers), and any other type of device that is used to cut hair (e.g. hair clippers), even if those devices do not necessary aim to provide a 'clean shave' (i.e. to remove hair at the level of the skin).

Figure 1:
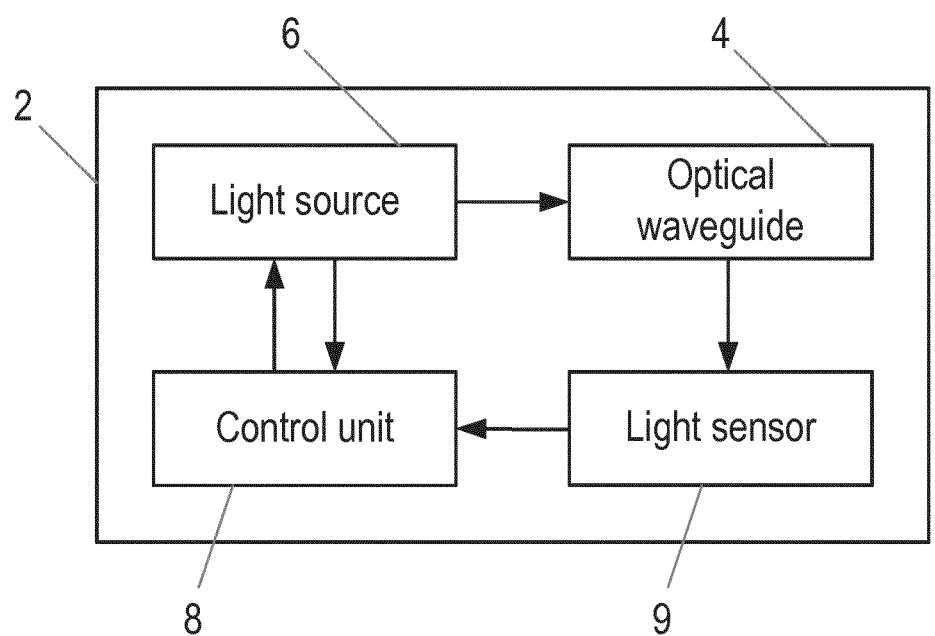
FIG. 1 is a block diagram of a hair cutting device according to an embodiment of the invention.
Figure 2:
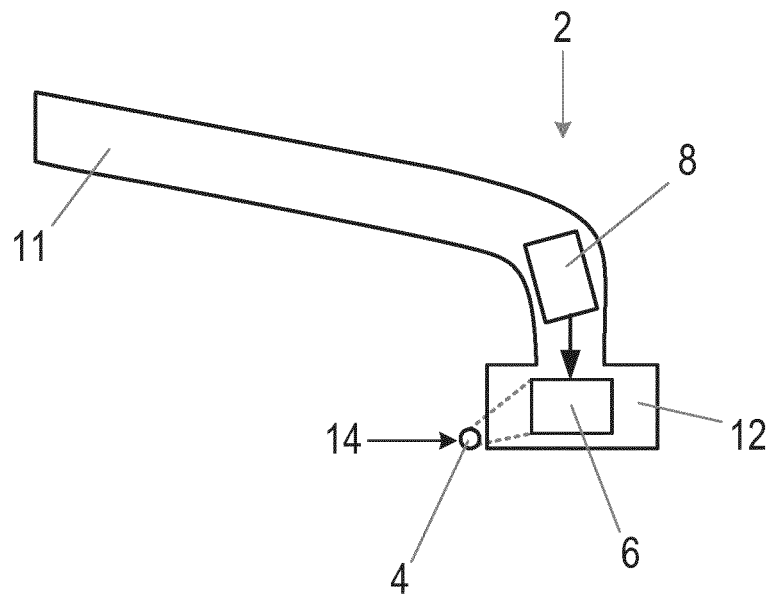
FIG. 2 is a pair of schematic drawings showing different views of an exemplary hair cutting device according to an embodiment of the invention.
Figure 2:
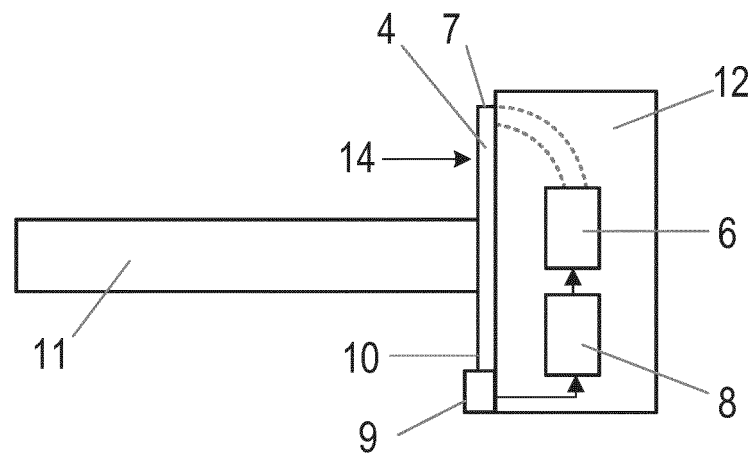

FIG. 1 is a block diagram of a hair cutting device 2 according to an embodiment of the invention. FIG. 2 shows a hair cutting device 2 in the form of a handheld razor according to an exemplary embodiment of the invention. The hair cutting device 2 is for cutting (e.g. shaving) hair on a body of a subject. The subject may be a person or an animal. The hair may be facial hair (i.e. hair on the subject's face), or hair on the subject's head or other part of their body (legs, chest, etc.).

The hair cutting device 2 comprises a cutting element 4 that enables hair to be cut as the hair cutting device 2 is moved over the skin of a subject. The cutting element 4 is an optical waveguide 4 that is arranged on the hair cutting device 2 so that the optical axis of the optical waveguide 4 (i.e. the line along which light typically propagates through the optical waveguide 4) is generally perpendicular to the direction in which the hair cutting device 2 is moved so that hairs contact the side wall of the optical waveguide 4 (the side wall corresponding to the long edge of the optical waveguide 4) as the hair cutting device 2 is moved across the skin of the subject. In some embodiments, the optical waveguide 4 is an optical fibre, although those skilled in the art will be aware of other types of optical waveguide that can be used according to the invention, such as a slab waveguide, a strip waveguide or a photonic crystal waveguide. An optical fibre comprises a core, and in some embodiments also comprises a cladding, which may or may not fully encompass the core (e.g. part of the core may be exposed).

A light source 6 is provided in the hair cutting device 2 that generates laser light at one or more specific wavelengths. The light source 6 is optically coupled to a first end 7 of the optical waveguide 4 so that the laser light generated by the light source 6 is coupled into the optical waveguide 4 (and specifically coupled into an end of the optical waveguide 4 so that the laser light propagates through the optical waveguide 4). The power (optical power) of the light generated by the light source 6 can be controlled in accordance with embodiments of the invention. In particular the power of the light can be controlled at least between a first power level that is sufficient to melt hair and a second power level that is low enough that it does not damage or irritate skin. The values of the first power level and the second power level depend on the specific properties of the optical waveguide 4, the wavelength of light and other properties of the light (e.g. pulse duration in the case of a pulsed mode of operation). However, a power level of less than 50 milliWatts (mW) may be considered safe for skin (i.e. it does not damage or irritate skin), while a power level above 50 mW may be effective for cutting/melting hairs, perhaps above 100 mW.

The light source 6 is configured to generate laser light at one or more specific wavelengths that can be used to cut or burn through hair. In particular, each wavelength corresponds to the wavelength of light absorbed by a chromophore that is found in or on hair. As is known, a chromophore is the part of a molecule that provides the molecule with its colour. Thus, the laser light will be absorbed by the chromophore and converted into heat which will melt or burn the hair or otherwise destroy the bonds in the molecules of the hair, and it is this melting or burning that provides the cutting action of the hair cutting device 2.

Suitable chromophores that can be targeted by the laser light generated by the light source 6 include, but are not limited to, melanin, keratin and water. Suitable wavelengths of laser light that can be used include, but are not limited to, wavelengths selected from the range 380 nm (nanometers) to 500 nm and 2500 nm to 3500 nm. Those skilled in the art will be aware of the wavelengths of light that are absorbed by these chromophores, and thus also the specific wavelengths of light that the light source 6 should generate for this purpose, and further details are not provided herein.

In some embodiments the light source 6 can be configured to generate laser light at a plurality of wavelengths (either simultaneously or sequentially), with each wavelength being selected to target a different type of chromophore. This can improve the cutting action of the optical waveguide 4 since multiple types of molecules in the hair may be burnt using the laser light. Alternatively multiple light sources 6 can be provided that each generate laser light at a respective wavelength, and each light source 6 can be coupled to a respective optical waveguide 4 to provide multiple cutting elements in the device 2.

The hair cutting device 2 also comprises a control unit 8 that controls the operation of the hair cutting device 2, and in particular is connected to the light source 6 to control the activation and deactivation of the light source 6, and the power of the light generated by the light source 6. The control unit 8 may activate and deactivate the light source 6 in response to an input from a user of the hair cutting device 2. In some embodiments, the control unit 8 can also receive an indication from the light source 6 of the power of the light generated by the light source 6. The control unit 8 can comprise one or more processors, processing units, multi-core processors or modules that are configured or programmed to control the hair cutting device 2. The control unit 8 can also comprise or be associated with a memory or memory module that stores data and computer readable code that is configured to be executed by the control unit 8 to cause the control unit 8 and hair cutting device 2 to operate according to the embodiments described herein.

In accordance with embodiments of the invention, the hair cutting device 2 also comprises a light sensor 9 that is for measuring the light level in the optical waveguide 4. It will be appreciated that the light level can be measured in terms of the light intensity, light power, light fluence, etc. The light sensor 9 can be any suitable type of sensor, for example a photodiode, photoresistor, phototransistor, etc. The output of the light sensor 9 is a signal indicating the light level in the optical waveguide 4 and this output can be used by the control unit 8 in combination with the light level input to the first end 7 of the optical waveguide 4 (which can be known, measured or calculated) to provide a measure of the amount of the input light that is transmitted across the optical waveguide 4. It will be appreciated that this measure is effectively a measure of the input light lost across (e.g. coupled out of) the optical waveguide 4. The light sensor 9 is coupled to the optical waveguide 4 away from the first end 7. For example the light sensor 9 can be coupled to the optical waveguide 4 at a second end 10 of the optical waveguide 4 (where the second end 10 is the opposite end of the optical waveguide 4 to the first end 7). Alternatively, the light sensor 9 can be coupled to the optical waveguide 4 between the first end 7 and the second end 10. In this case, the light sensor 9 can be coupled to the optical waveguide 4 so that at least part of a cutting face of the optical waveguide 4 is between the light sensor 9 and the first end 7.

As noted above, light is lost across the optical waveguide 4 due to coupling of light from the optical waveguide 4 into other objects, such as skin, hair and/or debris, (as well as natural losses as the light propagates through the optical waveguide 4) and these losses can be quantified using the measured light level and an indication of the input light level (i.e. the light level at the first end 7 of the optical waveguide 4). The light level that is input to the optical waveguide 4 (e.g. at the first end 7) may be known or measured, and thus it is possible to determine how much light is coupling out of (i.e. lost from) the optical waveguide 4 at a particular time. As noted above, the amount of light that couples out of or is lost from the optical waveguide 4 and into the other object depends in part on the size of the contact area between the optical waveguide 4 and the object, and thus an evaluation of the amount of light lost across the optical waveguide 4 (or an evaluation of the equivalent measure of the amount of light transmitted through the optical waveguide i.e. the amount of the input light that is not lost/coupled out from the optical waveguide 4) can provide an indication of whether the optical waveguide 4 is in contact with skin or hair. It will be appreciated that the indication of the light level at the first end 7 can be measured by a second light sensor 9 that is coupled to the optical waveguide 4 at the first end 7, or it can be derived by the control unit 8 from an indication of the power of the light generated by the light source 6 (e.g. an indication of the input current).

As noted above, FIG. 2 shows a hair cutting device 2 that is in the form of a handheld wet razor. FIG. 2 shows a side view and a bottom view of the razor 2. The razor 2 comprises a handle 11 for the subject (or other user of the device 2) to hold, and a head portion 12 that includes the cutting element 4 (optical waveguide/fibre). As shown, the optical waveguide 4 is arranged along an edge of the head portion, and a part of the optical waveguide 4 forms (or corresponds to) a cutting face 14. The cutting face 14 is the part of the optical waveguide 4 that is intended to come into contact with hair as the hair cutting device 2 is moved across the skin of the subject. A light source 6, control unit 8 and light sensor 9 (in the bottom view only) are shown as being incorporated into the head portion 12 and handle 11 respectively, but it will be appreciated that the positions of these components in the hair cutting device 2 as shown in FIG. 2 is not limiting. Likewise it will be appreciated that the embodiment shown in FIG. 2 is merely an example, and the cutting element 4, light source 6 and control unit 8 can be incorporated or used in place of a conventional blade in any type of hair cutting device 2 that conventionally comprises a blade for physically cutting or slicing hair (whether the blade is static or actuated in order to achieve a cutting action).

Figure 3:
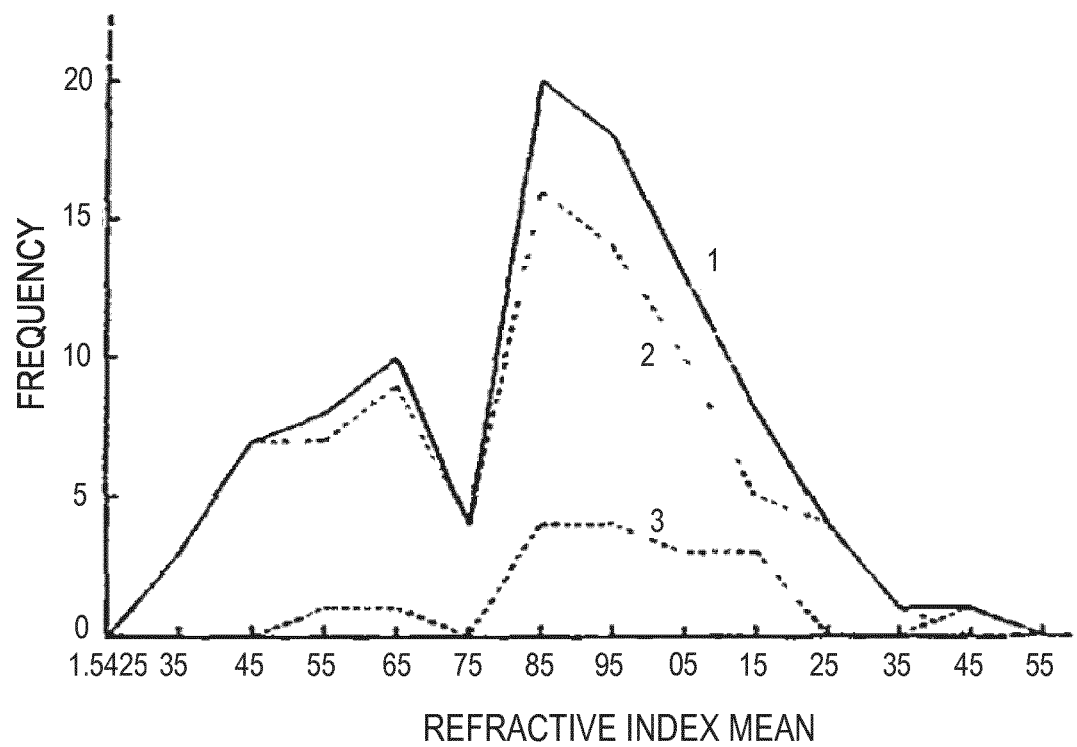
FIG. 3 is a graph illustrating the refractive index of hair.

The graph in FIG. 3 illustrates the refractive index of hair, which can be found in a paper by M. D. Greenwell, A. Willner, Paul L. Kirk: Human Hair Studies: III. Refractive Index of Crown Hair, 31 Am. Inst. Crim. L. & Criminology 746 (1940-1941). Curve 1 is a composite line, curve 2 is a line representing the refractive index for Caucasian people, and curve 3 is a line representing the refractive index for non-Caucasian people. Thus, it can be seen that the refractive index of hair is between (approximately) 1.545 and 1.555, although there will be variation between individuals. For example the above paper also recognises that the refractive index of hair can depend on the sex of the subject, e.g. the refractive index of hair on a female is generally higher than the refractive index of hair on a male.

As is known, the optical waveguide 4 acts as a waveguide for the light coupled from the light source 6 through the occurrence of total internal reflection, since the refractive index of air is lower than that of the optical waveguide 4. However, if an object that has a refractive index higher than the optical waveguide 4 is put into contact with the optical waveguide 4, then the total internal reflection is 'frustrated' and light can couple from the optical waveguide 4 into that object. Thus, in order for light to be coupled into a hair from the optical waveguide 4 (to provide the cutting action according to the invention), the optical waveguide 4 must have the same or a lower refractive index than hair at the point at which the hair contacts the optical waveguide 4. Thus, the optical waveguide 4 must have the same or a lower refractive index than hair at least at the cutting face 14 portion of the optical waveguide 4. Preferably the refractive index of the optical waveguide 4 at the cutting face 14 is the same as that of hair since that provides the best coupling of light from the optical waveguide 4 to the hair.

Thus, in some embodiments, the refractive index of the optical waveguide 4 at least at the cutting face 14 is equal to or lower than 1.56. More preferably the refractive index of the optical waveguide 4 at least at the cutting face 14 is equal to or lower than 1.55. Even more preferably, the refractive index of the optical waveguide 14 at least at the cutting face 14 is equal to or lower than 1.54, since this refractive index is below the refractive indices identified in FIG. 3.

In some embodiments, a lower bound for the refractive index of the optical waveguide 4 at the cutting face 14 can be 1.48, 1.51, 1.53 or 1.54.

A range of values from which the refractive index of the optical waveguide 4 is selected can be formed from any combination of the upper and lower refractive index bounds set out in the preceding paragraphs.

The optical waveguide/fibre 4 can be made from any suitable material or combination of materials. For example optical waveguides/fibres can be composed of or comprise silica, fluoride glass, phosphate glass, chalcogenide glass, and/or crown glass (such as BK7).

Figure 4:
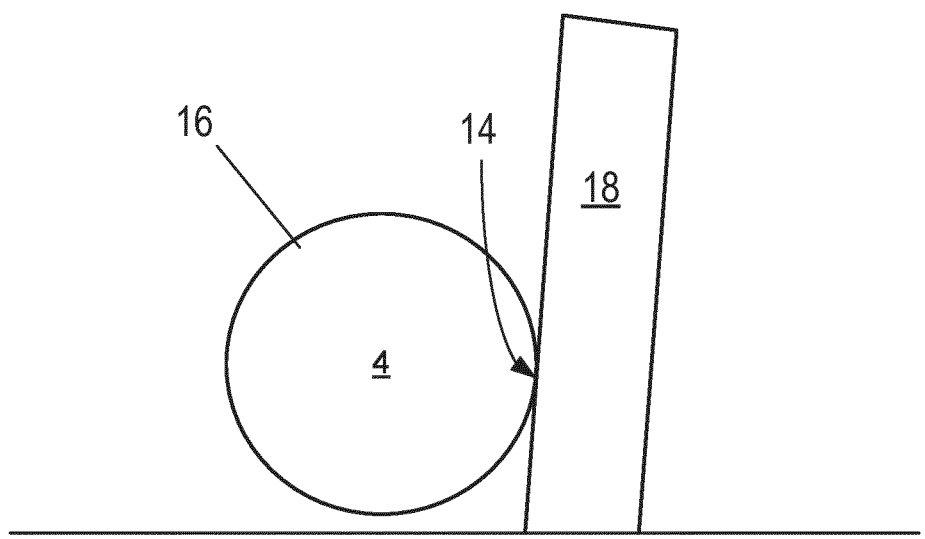
FIG. 4 is an illustration of an optical fibre cutting element.

FIG. 4 illustrates an exemplary embodiment of the optical waveguide 4. The optical waveguide 4 is for use in or with a hair cutting device 2, for example as shown in FIGS. 1 and 2. In FIG. 4 the optical waveguide 4 is shown side on (i.e. looking down the optical axis of the optical waveguide 4), and no other support element for the optical waveguide 4 is shown.

In FIG. 4, the optical waveguide 4 has a core 16. In this illustrated embodiment, the optical waveguide 4 does not include any cladding around the core 16. However it will be appreciated that in some embodiments the optical waveguide 4 can comprise cladding around the core 16, although preferably no cladding is present along the cutting face 14 (and indeed, in some embodiments the cutting face 14 can correspond to those parts of the optical waveguide 4 where there is no cladding).

The optical waveguide 4 is shown in contact with a hair 18 and close to, but not in contact with, the skin 20. The portion of the side wall of the core 16/optical waveguide 4 that is intended to contact hairs during use forms the cutting face 14. As described above, the refractive index of the core 16 is the same or lower than the refractive index of hair.

The core 16 may have a uniform refractive index (i.e. the same refractive index throughout the core 16), or it may be a graded index fibre, which means that the refractive index decreases with increasing distance from the optical axis.

As noted above, in order to cut hair effectively, the laser light needs to have sufficient power to cut the hair through melting. However, since the refractive index of skin is close to the refractive index of hair, light can couple into the skin if the cutting element 4 is brought into contact with the skin, and light at the power required to melt hair can irritate or burn the skin. As the measured light level (in combination with an input light level) can provide an indication of whether the optical waveguide 4 is in contact with skin or hair, in accordance with the invention the control unit 8 processes the output signal from the light sensor 9 to determine a measure of the input light lost/light transmitted across the optical waveguide 4 and controls the power of the light in the optical waveguide 4 on the basis of the determined measure.

Figure 5:
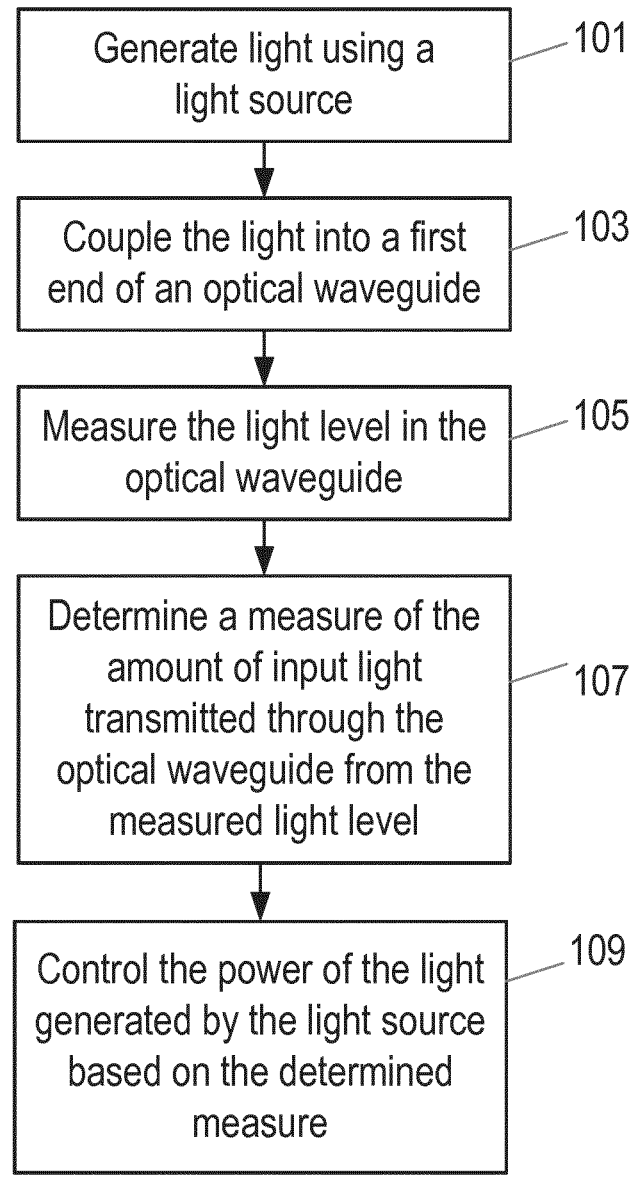
FIG. 5 is a flow chart illustrating a method of operating a hair cutting device according to an embodiment.

The flow chart in FIG. 5 illustrates a method of operating a hair cutting device 2 to cut hair on a body of a subject (e.g. hair on the head, face, neck, torso, arms or legs). In a first step, step 101, light is generated using a light source 6. The generated light is at one or more specific wavelengths corresponding to wavelengths absorbed by one or more chromophores in or on hair. The light is coupled from the light source 6 into a first end 7 of an optical waveguide 4 (step 103).

The light level in the optical waveguide 4 is measured using a light sensor 9 that is coupled to the optical waveguide 4 (step 105). As noted above, the light sensor 9 is coupled to the optical waveguide 4 away from the first end 7, for example at second end 10.

The control unit 8 receives the measurement of the light level from the light sensor 9 and determines a measure of the amount of input light transmitted across the optical waveguide 4 (or the equivalent measure of the amount of input light lost across the optical waveguide 4) from the measured light level (step 107). The measure of the input light lost/transmitted across the optical waveguide 4 is determined from the light level input at the first end 7 of the optical waveguide 4 and the light level measured by the light sensor 9 away from the first end 7. As noted above, the input light level can be measured by a second light sensor coupled to the first end 7 of the optical waveguide 4 or be indicated by the light source 6 to the control unit 8.

The measure of the input light lost/transmitted across the optical waveguide 4 can be determined in a number of different ways. In some embodiments, the control unit 8 calculates the amount of light lost/transmitted through the optical waveguide 4 as the ratio of the measured light level to the input light level (e.g. measured power to input power). This ratio (which will have a value between 0 and 1) indicates the proportion of the input light that is transmitted through the optical waveguide 4, and thus also indicates the proportion of light that is lost/coupling out of the optical waveguide 4. Alternatively, the measure of the light lost/ transmitted across the optical waveguide 4 can be determined by subtracting the measured light level from the input light level, or by using any other mathematical operation that provides a measure of the difference between the input light level and the measured light level and thus quantifies the amount of input light transmitted or the amount of input light lost.

The control unit then controls the power of the light generated by the light source based on the determined measure (step 109).

Step 109 can comprise the control unit 8 comparing the determined measure to one or more thresholds and controlling the power of the generated light accordingly.

The change in the power level can be effected by a change in the absolute power level, or, where the light source 6 operates in a pulsed mode of operation and generates pulses of light, the change in power level can be effected by a change in the peak power level and/or by a change in the duty cycle of the light pulse (e.g. by increasing or decreasing the fraction of time that the light is on).

Figure 6:
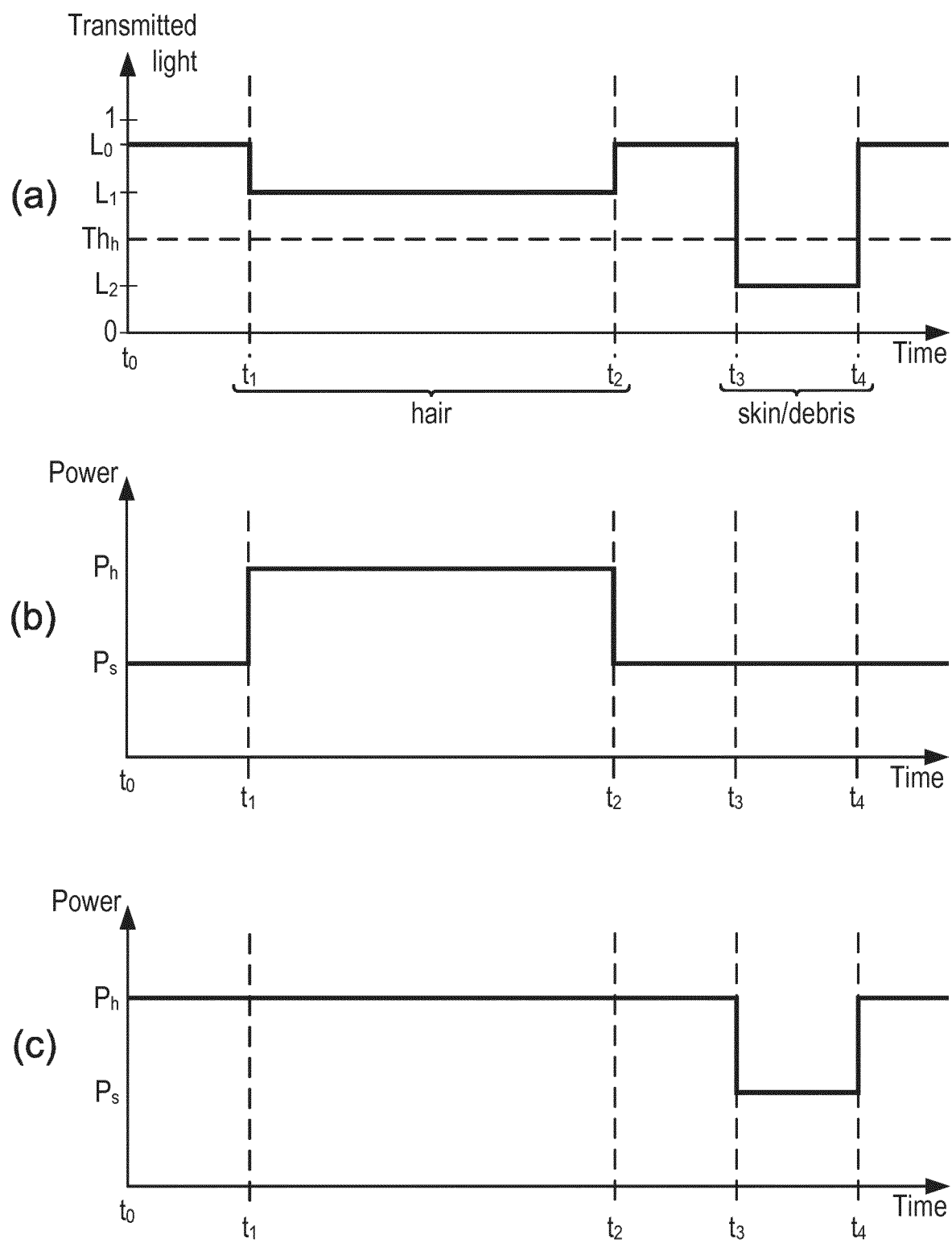
FIG. 6 is a set of graphs illustrating the adjustment of the power of a light source based on a measured light level.

The graphs in FIG. 6 illustrate examples of how the power of the generated light can be controlled according to the measured light level, and in particular according to the measure of the input light transmitted through/lost across the optical waveguide 4.

FIG. 6(a) shows the measure in terms of the input light transmitted through the optical waveguide 4 over time as the hair cutting device 2 is used to cut hair on a subject. In this example, the measure is given by the ratio of the light level measured by the light sensor 9 to the input light level (as measured by a second light sensor or calculated or obtained by the control unit 8). As such, the amount of light transmitted through the optical waveguide 4 has a value between 0 (representing all light coupling out of the optical waveguide 4/no light transmitting through the optical waveguide 4) and 1 (which would represent the ideal case of all input light transmitting through the waveguide 4/no light coupling out of the optical waveguide 4 and no light losses in the waveguide 4) At time $t_0$ the light source 6 is controlled by the control unit 8 to generate light at the required wavelength or wavelengths, and the light level in the optical waveguide 4 is measured by the light sensor 9. The measure is referred to below as the transmission measure.

Initially, the optical waveguide 4 is not in contact with hair or skin (or debris or other skin features such as a mole), and the transmission measure will be at an initial level $L_0$, which should correspond to the proportion of light transmitted through the optical waveguide 4 when no light (or a minimum amount of light) is coupling out of the optical waveguide 4 (i.e. $L_0$ is close to 1).

At a time $t_1$, the optical waveguide 4 is moved into contact with hair and some of the light in the optical waveguide 4 couples into the hair. The light level measured by the light sensor 9 will therefore decrease, and the transmission measure will also decrease, which is shown in FIG. 6(a) as $L_1$ which is lower than the initial transmission/loss measure level $L_0$.

Later, at a time $t_2$ the optical waveguide 4 is no longer in contact with hair (or any other object), and thus no light (or the minimum amount of light) is coupling out of the optical waveguide 4. The transmission measure is therefore $L_0$.

The optical waveguide 4 is subsequently brought into contact with the skin 20 of the subject (or another skin feature such as a mole) at time $t_3$ until time $t_4$ and light couples into the skin 20. Due to the larger contact area, the amount of light that couples into the skin is higher than when the optical waveguide 4 is in contact with the hair between times $t_1$ and $t_2$, and thus the transmission measure is lower between times $t_3$ and $t_4$ than between times $t_1$ and $t_2$. The transmission measure between times $t_3$ and $t_4$ is labelled $L_2$ in FIG. 6(a).

At time $t_4$ the optical waveguide 4 is no longer in contact with the skin and the amount of light transmitted through the optical waveguide 4 is again $L_0$.

It will be appreciated that the y-axis in FIG. 6(a) is not drawn to scale, and the distribution of (i.e. spacing between) $L_0$, $L_1$ and $L_2$ between 0 and 1 may be different to that shown.

In accordance with some embodiments, a threshold value $Th_h$ is used by the control unit 8 to distinguish whether the optical waveguide 4 is in contact with hair or skin. The threshold value $Th_h$ has a value between 0 and 1. In particular, if the transmission measure has decreased below the threshold value $Th_h$ then the control unit 8 can determine that the optical waveguide 4 is in contact with skin (since the amount of light coupling out of the optical waveguide 4 is relatively high). If the transmission measure has decreased below the initial amount of light transmitted through the optical waveguide 4 $L_0$ (indicating some coupling of light) but is above the threshold value $Th_h$, then the control unit 8 can determine that the optical waveguide 4 is in contact with hair (since the amount of light coupling out of the optical waveguide 4 is relatively low, at least compared to coupling to skin).

It will be appreciated that in some embodiments the control unit 8 can compare the current transmission measure to an initial transmission measure (e.g. $L_0$) to determine if the amount of light transmitted through the optical waveguide 4 has decreased or is below the initial level, or the control unit 8 can compare the current transmission measure to a default or predetermined transmission measure corresponding to the amount of light transmitted through the optical waveguide 4 when the optical waveguide 4 is known to not be in contact with any object (i.e. skin or hair), and which therefore, indicates the losses that take place within the optical waveguide 4. It will be appreciated that in some embodiments the control unit 8 may require at least a minimum decrease in the transmission measure before determining that the optical waveguide 4 is in contact with hair in order to avoid small changes or fluctuations in the amount of light transmitted through the optical waveguide 4 leading to the control unit 8 determining that the optical waveguide 4 is in contact with hair.

The threshold $Th_h$ is shown in FIG. 6(a), and thus it can be seen that the amount of light transmitted through the optical waveguide 4 between times $t_1$ and $t_2$ is lower than the initial amount of light transmitted through the optical waveguide 4 $L_0$ and higher than $Th_h$ and the amount of light transmitted through the optical waveguide 4 between times $t_3$ and $t_4$ is lower than $Th_h$. At other times the amount of light transmitted through the optical waveguide 4 is $L_0$ and thus above $Th_h$.

The graph in FIG. 6(b) illustrates a first exemplary way of controlling the power of the light generated in accordance with the invention. In this example, if the control unit 8 determines from the measured light level that the optical waveguide 4 is not in contact with any object (i.e. hair or skin), the control unit 8 controls the light source 6 to generate light at a power level that does not burn or irritate skin. This helps to maximise the battery life of the hair cutting device 2 since power is not wasted producing high power light when no hair cutting action is required. The power level that does not burn or irritate skin is indicated as $P_s$ in FIG. 6(b). If the control unit 8 determines from the measured light level and input light level that the optical waveguide 4 is in contact with skin, the control unit 8 controls the light source 6 to generate light at the power level $P_s$ that does not burn or irritate skin. However, if control unit 8 determines from the measured light level and the input light level that the optical waveguide 4 is in contact with hair, the control unit 8 controls the light source 6 to generate light at a power level that can burn or melt hair. This power level is indicated as $P_h$ in FIG. 6(b), and is a higher power than $P_s$.

Thus, based on the transmission measure shown in FIG. 6(a), the control unit 8 controls the light source 6 to generate light with power $P_s$ (so safe for skin) when the transmission measure is $L_0$ (i.e. an initial amount of input light is transmitted through the optical waveguide 4) between times $t_0$ and $t_1$, $t_2$ and $t_3$, and $t_4$ onwards. The control unit 8 also controls the light source to generate light with power $P_s$ when the transmission measure is below $Th_h$ (i.e. between times $t_3$ and $t_4$). However, when the transmission measure is below the initial transmission measure $L_0$ and above $Th_h$, indicating that the optical waveguide 4 is in contact with hair, the control unit 8 controls the light source 6 to increase the optical power of the generated light to $P_h$ in order to cut (melt) the hair. The control unit 8 maintains the power at $P_h$ while the transmission measure indicates that the optical waveguide 4 is in contact with hair. At time $t_2$ the transmission measure increases to $L_0$, which can occur when the optical waveguide 4 has cut the hair, or otherwise moved out of contact with the hair, and the control unit 8 controls the light source 6 to reduce the light power to $P_s$.

The graph in FIG. 6(c) illustrates a second exemplary way of controlling the power of the light generated in accordance with the invention. In this example, the control unit 8 controls the light source 6 to generate light at a power level that is sufficient to melt hair ($P_h$) except when the control unit 8 determines from the measured light level and the input light level that the optical waveguide 4 is in contact with skin (or other skin features such as a mole). Thus, as shown in FIG. 6(c) the power of the generated light is set to $P_h$ except between times $t_3$ and $t_4$ where the amount of light transmitted through the optical waveguide 4 is below $Th_h$. This embodiment has the advantage that the hair cutting device 2 is ready to cut hair as soon as it comes into contact with the optical waveguide 4.

In further embodiments, the control unit 8 can be configured to detect the presence of debris on the optical waveguide 4 separate to detecting that the optical waveguide 4 is in contact with the skin of the subject. This embodiment is useful as it enables the control unit 8 to determine if the optical waveguide 4 needs to be cleaned or replaced. This embodiment is explained with reference to FIG. 7.

In particular, the presence of debris on the optical waveguide 4, such as cut hairs or shaving fluids, etc., will result in light coupling into the debris and a decrease in the measured light level. The decrease in the transmission measure can be relatively large as the area of contact with the optical waveguide 4 can be extensive, e.g. typically an order of magnitude or more than for hair, and perhaps of the same order as for skin or other features such as moles. However in contrast to contact with hair, skin or skin features, the transmission measure will not increase (i.e. return to an initial transmission measure) after a short period of time, and in particular the transmission measure will remain at the lower amount even when the hair cutting device 2 is subsequently activated.

Figure 7:
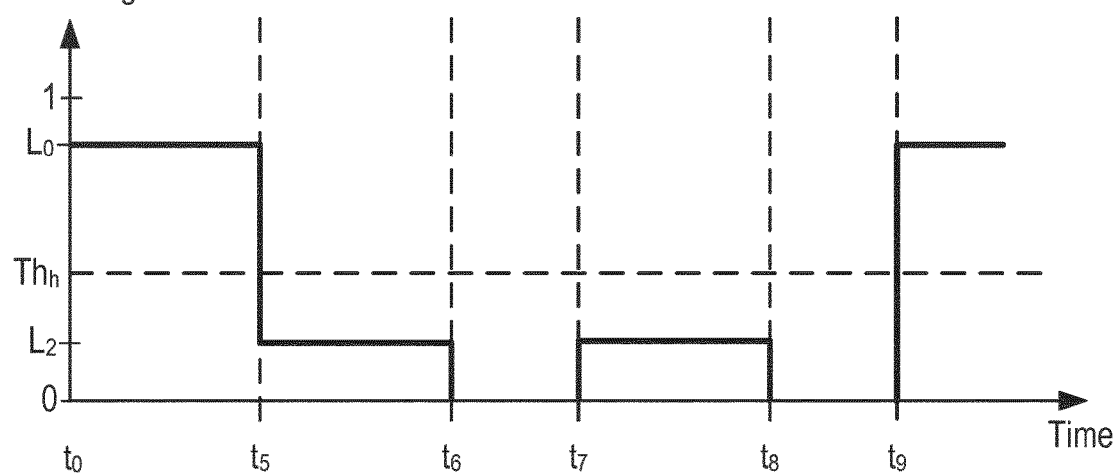
FIG. 7 is a graph illustrating the detection of debris on an optical waveguide according to an embodiment.

Therefore, with reference to FIG. 7, initially (at $t_0$) the transmission measure is $L_0$, as in FIG. 6(a), indicating that the optical waveguide 4 is not in contact with hair, skin or debris. At some time, $t_5$, there is debris on the optical waveguide 4 and this results in the transmission measure decreasing to $L_2$ due to light coupling into the debris. This transmission measure $L_2$ is below the threshold $Th_h$ and so the control unit 8 will control the light source 6 to generate light with a low power that does not damage skin (e.g. $P_s$ as described above).

Once the debris is present on the optical waveguide 4, the transmission measure will not significantly vary, and thus the transmission measure remains at $L_2$ until the hair cutting device 2 is deactivated and the light source 6 is switched off (or otherwise does not generate light) at time $t_6$. When the hair cutting device 2 is subsequently activated (or the light source 6 otherwise starts to generate light again) at time $t_7$, the transmission measure will still be $L_2$ due to the presence of the debris on the optical waveguide 4. The control unit 8 can therefore determine that there is debris on the optical waveguide 4 by comparing the transmission measure on activation to a default or predetermined initial transmission measure (e.g. $L_0$). If the comparison indicates that the transmission measure is low compared to the default or predetermined initial transmission measure then the control unit 8 can determine that there is debris on the optical waveguide 4. The control unit 8 can optionally deactivate the device 2 again (as shown at time $t_8$). The control unit 8 can also output an indication to a user of the device 2 that the optical waveguide 4 needs to be cleaned (or replaced). The user can then clean the optical waveguide 4 and then reactivate the device 2. If the cleaning is successful, the transmission measure when the device 2 is activated (e.g. at time $t_9$) will be back to the normal initial transmission measure, e.g. $L_0$. If the cleaning is unsuccessful (e.g. the transmission measure when the device 2 is activated again is still low (e.g. $L_2$), then the control unit 8 can output an indication to the user that the optical waveguide/cutting element 4 needs to be replaced.

In further embodiments, to further improve the ability of the control unit 8 to determine whether a low transmission measure in the optical waveguide 4 is due to skin contact or debris, the hair cutting device 2 can include a sensor that measures the movement of the hair cutting device 2 or the speed of movement of the hair cutting device 2 on the user, and the control unit 8 can use the measured speed to estimate the likelihood that the low transmission measure is due to skin contact or debris.

Debris on the optical waveguide 4 tends to be static or slow moving. A slowly varying low transmission measure in the time domain can thus be due to debris, except where the optical waveguide 4 is touching hair or skin in the same manner for a long time. However, this can only occur if the device 2 is moving slowly relative to the skin and hair. Thus, the measured speed can be used to infer whether a slowly varying low transmission measure may be due to debris or just a slow hair cutting movement. Thus, a low measured transmission measure (e.g. less than $Th_h$), combined with a relatively low speed of movement (e.g. movement speed less than a threshold), can indicate that the low transmission measure may be due to contact between the optical waveguide 4 and the skin, while a low transmission measure (e.g. less than $Th_h$) combined with a relatively high speed of movement (e.g. movement speed more than the threshold), can indicate that the low transmission measure is due to debris on the optical waveguide 4.

The movement sensor can measure the movements of the hair cutting device 2 and a speed or velocity of the hair cutting device 2 can be determined from the measurements. The movement sensor provides an output signal representing the measured movements to the control unit 8. The movements that are relevant are the movements of the hair cutting device 2 in the direction in which the device 2 moves to cut hairs (e.g. in a direction perpendicular to the side wall of the optical waveguide 4 and in a plane parallel to the skin surface), and specifically the speed of movement in this direction. Depending on the type of movement sensor in the device 2, the output signal from the movement sensor can provide an indication of the speed or velocity itself, or the output signal can provide measurements of the movement that can be processed or analysed by the control unit 8 to determine the speed or velocity.

In some embodiments, the movement sensor is an accelerometer that measures the accelerations of the hair cutting device 2 and that outputs a signal to the control unit 8 that represents the measured accelerations. As only the speed of movement in a particular direction is required, the accelerometer can be a one-dimensional accelerometer that is oriented in the hair cutting device 2 so that it measures the accelerations in the required direction. The control unit 8 can integrate this measured acceleration with respect to time to determine the speed or velocity in the required direction. Alternatively the accelerometer can measure accelerations in two or three dimensions, and the control unit 8 can process this acceleration signal to determine the velocity or speed in the required direction (e.g. by integrating the acceleration with respect to time and filtering the measurements to extract the speed or velocity in the required direction).

In alternative embodiments, the movement sensor can be an optical movement sensor, wheel sensor or ball sensor (for example as used in computer mice) that measure movements of the hair cutting device 2 with respect to a surface (e.g. the skin) and that outputs a signal to the control unit 8 that represents the measured speed or velocity. As known to those skilled in the art, an optical movement sensor comprises a light source (separate to light source 6) for illuminating the surface (e.g. skin) and one or more light sensors (separate to light sensor 9), such as a photodiode, a photoresistor or a phototransistor, for measuring the reflected light and thus detecting movement of the hair cutting device 2 relative to the skin.

There is therefore provided an improved hair cutting device that reduces the risk of damage or injury to the skin of the subject and that maintains hair cutting effectiveness.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A hair cutting device for cutting hair on a body of a subject, the hair cutting device comprising:
    a light source for generating light at one or more specific wavelengths corresponding to wavelengths absorbed by one or more chromophores in or on hair;
    a cutting element that comprises an optical waveguide that is coupled at a first end to the light source to receive light, wherein a portion of a sidewall of the optical waveguide forms a cutting face for contacting hair;
    a light sensor that is coupled to the optical waveguide away from the first end, wherein the light sensor is for measuring the light level in the optical waveguide and for providing an output signal representing the measured light level; and
    a control unit that is coupled to the light source, and coupled to the light sensor to receive the output signal, wherein the control unit is configured to determine a measure of the amount of input light transmitted across the optical waveguide from the measured light level and an input light level at the first end of the optical waveguide, wherein the measure of the amount of input light transmitted across the optical waveguide is an indication of whether the optical waveguide is in contact with hair, skin or debris; and to control the power of the light generated by the light source based on the indication of whether the optical waveguide is in contact with hair, skin or debris.

2. A hair cutting device as claimed in claim 1, wherein the control unit is configured to set the power of the light generated by the light source to a first power level if the determined measure is above a threshold value, and to set the power of the light generated by the light source to a second power level if the determined measure is less than the threshold value, wherein the first power level is higher than the second power level.

3. A hair cutting device as claimed in claim 2, wherein the control unit is configured to set the power of the light generated by the light source to the first power level if the determined measure is equal to an amount of input light transmitted across the optical waveguide when the optical waveguide is not in contact with hair, skin or debris.

4. A hair cutting device as claimed in claim 2, wherein the control unit is configured to set the power of the light generated by the light source to the second power level if the determined measure is equal to an amount of input light transmitted across the optical waveguide when the optical waveguide is not in contact with hair, skin or debris.

5. A hair cutting device as claimed in claim 2, wherein the first power level corresponds to a power level required to melt hair and the second power level corresponds to a power level that does not irritate or burn skin.

6. A hair cutting device as claimed in claim 1, further comprising:
 a movement sensor for measuring the speed of movement of the hair cutting device;
 wherein the control unit is configured to determine if debris is present on the optical waveguide based on the determined measure and the measured speed of movement.

7. A hair cutting device as claimed in claim 1, wherein the control unit is configured to receive the input light level at the first end of the optical waveguide from a second light sensor at the first end or an indication of the input light level at the first end from the light source.

8. A method of operating a hair cutting device to cut hair on a body of a subject, the hair cutting device comprising a cutting unit that comprises an optical waveguide, wherein a portion of a sidewall of the optical waveguide forms a cutting face for contacting hair, the method comprising:
 generating light using a light source at one or more specific wavelengths corresponding to wavelengths absorbed by one or more chromophores in or on hair;
 coupling the light from the light source into a first end of the optical waveguide;
 measuring the light level in the optical waveguide using a light sensor that is coupled to the optical waveguide away from the first end;
 determining a measure of an amount of input light transmitted through the optical waveguide from the measured light level and an input light level at the first end of the optical waveguide, wherein the measure of the amount of input light transmitted across the optical waveguide is an indication of whether the optical waveguide is in contact with hair, skin or debris; and
 controlling the power of the light generated by the light source based on the indication of whether the optical waveguide is in contact with hair, skin or debris.

9. A method as claimed in claim 8, wherein the step of controlling the power of the light comprises setting the power of the light generated by the light source to a first power level if the determined measure is above a threshold value, and setting the power of the light generated by the light source to a second power level if the determined measure is less than the threshold value, wherein the first power level is higher than the second power level.

10. A method as claimed in claim 9, wherein the step of controlling the power of the light comprises setting the power of the light generated by the light source to the first power level if the determined measure is equal to an amount of input light transmitted across the optical waveguide when the optical waveguide is not in contact with hair, skin or debris.

11. A method as claimed in claim 9, wherein the step of controlling the power of the light comprises setting the power of the light generated by the light source to the second power level if the determined measure is equal to an amount of input light transmitted across the optical waveguide when the optical waveguide is not in contact with hair, skin or debris.

12. A method as claimed in claim 9, wherein the first power level corresponds to a power level required to melt hair and the second power level corresponds to a power level that does not irritate or burn skin.

13. A method as claimed in claim 8, the method further comprising the step of:
 measuring the speed of movement of the hair cutting device using a movement sensor; and
 wherein the method comprises determining if debris is present on the optical waveguide based on the determined measure and the measured speed of movement.

14. A method as claimed in claim 8, wherein the method further comprises the step of:
 receiving the input light level at the first end of the optical waveguide from a second light sensor at the first end or an indication of the input light level at the first end from the light source.

15. A computer program product comprising a non-transitory, computer readable medium having computer readable code embodied therein, the computer readable code being configured such that, on execution by a suitable computer, processor or control unit, the computer, processor or control unit is caused to perform the method of claim 8.

* * * * *